(12) United States Patent
Yokoo et al.

(10) Patent No.: US 11,607,425 B2
(45) Date of Patent: *Mar. 21, 2023

(54) KIDNEY PRODUCTION METHOD (71) Applicants: Takashi Yokoo, Tokyo (JP); BIOS Co., Ltd, Tokyo (JP)

(72) Inventors: Takashi Yokoo, Tokyo (JP); Shuichiro Yamanaka, Tokyo (JP)

(73) Assignees: Takashi Yokoo, Tokyo (JP); BIOS Co., Ltd, Tokyo (JP)

( * ) Notice: Subject to any disclaimer, the term of this patent is extended or adjusted under 35 U.S.C. 154(b) by 1082 days.

This patent is subject to a terminal disclaimer.

(21) Appl. No.: 16/313,253

(22) PCT Filed: Jun. 8, 2017

(86) PCT No.: PCT/JP2017/021310
§ 371 (c)(1),
(2) Date: May 13, 2019

(87) PCT Pub. No.: WO2018/003451
PCT Pub. Date: Jan. 4, 2018

(65) Prior Publication Data
US 2019/0269733 A1 Sep. 5, 2019

(30) Foreign Application Priority Data
Jun. 29, 2016 (JP) .............. JP2016-129391

(51) Int. Cl.
| | |
|---|---|
| *A61L 27/36* | (2006.01) |
| *A61K 35/22* | (2015.01) |
| *A61P 13/12* | (2006.01) |
| *C12N 5/071* | (2010.01) |
| *A01K 67/027* | (2006.01) |
| *A61L 27/38* | (2006.01) |
| *C12N 15/09* | (2006.01) |

(52) U.S. Cl.
CPC ............ *A61K 35/22* (2013.01); *A01K 67/027* (2013.01); *A61L 27/36* (2013.01); *A61L 27/38* (2013.01); *A61P 13/12* (2018.01); *C12N 5/0686* (2013.01); *C12N 15/09* (2013.01)

(58) Field of Classification Search
CPC ........................ A61K 35/22; A61L 2430/26
USPC ....................................................... 424/93.7
See application file for complete search history.

(56) References Cited

U.S. PATENT DOCUMENTS

| 7,074,552 B1 | 7/2006 | Nigam et al. | |
| 2006/0147429 A1* | 7/2006 | Diamond | ........... A01K 67/0271 424/93.7 |
| 2011/0104656 A1* | 5/2011 | Kobayashi | ........... C12N 5/0686 435/1.3 |

FOREIGN PATENT DOCUMENTS

| CN | 101679950 A | 3/2010 |
| CN | 102105581 A | 6/2011 |
| CN | 109642210 A | 4/2019 |
| WO | WO 2004/027029 A2 | 4/2004 |
| WO | WO 2006/074012 A2 | 7/2006 |
| WO | WO 2008151254 A1 | 12/2008 |
| WO | WO 2014138486 A1 | 9/2014 |
| WO | WO 2016/098620 A1 | 6/2016 |

OTHER PUBLICATIONS

Khan (2014, J Artif Organs, 17:291-300).*
Chinese Office Action for Chinese Patent Application No. 201780051066.5, dated Oct. 27, 2021.
Usui et al., "Generation of Kidney from Pluripotent Stem Cells via Blastocyst Complementation", The American Journal of Pathology, Jun. 2012, 180(6): 2417-2426.
Yamanaka et al, "Current Bioengineering Methods for Whole Kidney Regeneration", Stem Cells International, 2015.
Yamanaka et al, "Generation of interspecies limited chimeric nephrons using a conditional nephron progenitor cell replacement system", Nature Communications, 2017.
Zhang et al, "In vivo regeneration of renal vessels post whole decellularized kidneys transplantation", Oncotarget, 2015, 6(38): 40433-40442.
Japanese Notice of reasons for Rejection in Japanese Patent Application No. 2020-209590, dated Jan. 21, 2022.
Yokoo et al., "Xenobiotic Kidney Organogenesis from Human Mesenchymal Stem Cells Using a Growing Rodent Embryo", American Society of Nephrology, 2006, 17: 1026-1034.
Kemter et al., "Pigs pave a way to de novo formation of functional human kidneys: Fig. 1." Proceedings of the National Academy of Science, vol. 112, No. 42, Oct. 12, 2015, p. 12905-12906, XP55265799, ISSN: 0027-8424, DOI: 10.1073/pnas.1517582112.
Michos et al., "Kidney development: from ureteric bud formation to branching morphogenesis", Current Opinion in Genetics & Development, Current Biology LTD, XX, vol. 19, No. 5, Oct. 1, 2009, pp. 484-490, XP026736034, ISSN: 0959-437X, DOI: 10.1016/J.GDE.2009.09.003 [retrieved on Oct. 14, 2009].
Steer et al., "Developmental approaches to kidney tissue engineering", American Journal of Physiology: Renal Physiology, vol. 286, No. 1, Jan. 1, 2004, pp. F1-F7, XP055450157, ISSN: 1931-587X, DOI: 10.1152/ajprenal.00167.2003.
Supplementary European Search Report in related Application No. EP 17 81 9816, dated Jan. 7, 2020 (8 pages).
Grgic, I. et al., (2012) "Targeted proximal tubule injury triggers interstitial fibrosis and glomerulosclerosis," Kidney International, 82:172-183.

(Continued)

Primary Examiner — Valarie E Bertoglio
(74) Attorney, Agent, or Firm — Lathrop GPM LLP; Brian C. Trinque (57) ABSTRACT

The present invention provides a kidney production method including a step of tissue-specifically removing a metanephric mesenchyme of a metanephros of a non-human animal; a step of transplanting a human kidney precursor cell into the metanephros; and a step of advancing development of the metanephros, which is a step in which the transplanted human kidney precursor cell is differentiated and matured to form a part of the kidney.

3 Claims, 6 Drawing Sheets

(56) References Cited

OTHER PUBLICATIONS

International Search Report for PCT/JP2017/021301 dated Aug. 29, 2017.
Kaku, Y. et al., (2012) "From kidney development toward regeneration", Journal of Japanese Biochemical Society, 84(12):985-993.
Matsumoto, K. et al., (2012) "Xenotransplanted Embryonic Kidney Provides a Niche for Endogenous Mesenchymal Stem Cell Differentiation Into Erythropoietin-Producing Tissue," Stem Cells, 30:1228-1235.
Sharmin, S. et al., (2016) "Human Induced Pluripotent Stem Cell-Derived Podocytes Mature into Vascularized Glomeruli upon Experimental Transplantation," J. Am, Soc. Nephrol., 27:1778-1791, Epub 2015, Nov. 19, ISSN:1046-6673/2706-1778.
Song, R. et al., (2012) "Targeted Inactivation of the Prorenin Receptor (PRR) in the Ureteric Bud (UB) Inhibits UB Branching Morphogenesis and Collecting Duct Development," J. Am. Soc. Nephrol., Kidney Week 2012 Abstract Supplement, 23:9, 9A, TH-OR042.
Takasato, M. et al., (2014) "Directing human embryonic stem cell differentiation towards a renal lineage generates a self-organizing kidney," Nat. Cell Biol., 16(1):118-126.
Yokoo, T. (2013) "Rinsho Oyo ni Muketa Jinzo Saisei Kenkyu-Dai 58 kai The Japanese Society for Dialysis Therapy Kyoiku Koen yori-", Toseki Kaishi, 46(11):1055-1060.
Yokoo, T. (2014) Taisei Soshiki Niche-ho ni yoru Seitai Kansaibo Yudogata Zoki Saisei Shugi no Kaihatsu, Kaken Kagaku Kenkyuhi Josei Jigyo Database Nendo Jisshi Jokyo Hokokusho [Online], May 27, 2016 (May 27, 2016), [retrieval date Aug. 14, 2017 (Aug. 14, 2017)], Internet: <URL https://kaken.nii.ac.jp/ja/report/KAKENHI-PROJECT-25461235/254612352014hokoku/>.
Yokoo, T. (2015) "CKD and Regenerative Medicine", The Journal of the Japanese Society of Internal Medicine, 104(3):600-606.
Yokote, S. et al., (2015) "Urine excretion strategy for stem cell-generated embryonic kidneys," Proc. Natl. Acad. Sci. USA, 112(42)12980-12985.
"Animal Development Revised Edition", Editor-in-chief: Li Yunlong, Liu Chunqiao, Shandong Science and Technology Press, "The General Process of Kidenogensis 24.3.1 ", pp. 348-349, May 31, 2005.
International Search Report for PCT/JP2017/021352, dated Aug. 29, 2017, 5 pages.
European Search Report for EP Application No. 17819817.2, dated Jan. 3, 2020, 6 pages.
Chinese Office Action for Chinese Patent Application No. 201780051181.2, dated Apr. 26, 2022, 16 pages.

* cited by examiner

KIDNEY PRODUCTION METHOD

RELATED APPLICATIONS

This application is a 35 U.S.C. § 371 filing of International Patent Application No. PCT/JP2017/021310, filed Jun. 8, 2017, which claims priority to Japanese Patent Application No. 2016-129391, filed Jun. 29, 2016, the entire disclosures of which are hereby incorporated herein by reference.

TECHNICAL FIELD

The present invention relates to a kidney production method. More specifically, the present invention relates to a kidney production method, a kidney, a non-human animal, an organ for transplantation, a kit for kidney production, and a medical drug for kidney regeneration.

BACKGROUND ART

Due to aging and expansion of an adaptation disease, dialysis patients are increasing rapidly. The lives of these patients can be saved by dialysis medical treatment, but because dialysis does not compensate for all kidney functions, cardiovascular diseases of the patients tend to increase, thereby causing rise in mortality rates. In addition, the dialysis patients are overburdened with time and mental loads, which makes it difficult to return to society in many cases.

Furthermore, there are about 2 million patients with the end-stage renal disease requiring a kidney transplantation, and the number of patients tends to further increase due to the organ donor shortage. Therefore, the end-stage renal disease is a serious medical problem.

At present, various tissue-specific precursor cells or tissue stem cells can be induced from pluripotent stem cells such as iPS cells and ES cells (refer to, for example, Non-Patent Document 1). However, for example, the kidney is an organ with low self-repairing ability, and therefore the kidney function depends on a complicated structure composed of various kinds of cells. For this reason, current techniques have not yet reached a stage where kidneys having complicated three-dimensional structures can be regenerated from kidney precursor cells.

CITATION LIST

Non-Patent Literature

[Non-Patent Document 1] Takasato M, et al., Directing human embryonic stem cell differentiation towards a renal lineage generates a self-organizing kidney, Nat. Cell Biol., 16 (1), 118-126, 2014.

SUMMARY OF INVENTION

Technical Problem

An object of the present invention is to provide a technique for producing a kidney from kidney precursor cells.

Solution to Problem

The present invention includes the following aspects.

(1) A kidney production method including: a step of tissue-specifically removing a metanephric mesenchyme of a metanephros of a non-human animal; a step of transplanting a human kidney precursor cell into the metanephros; and a step of advancing development of the metanephros, in which the transplanted human kidney precursor cell is differentiated and matured to form a part of the kidney.

(2) The kidney production method according to (1), further including: a step of tissue-specifically removing an ureteric bud of the metanephros; and a step of transplanting a human kidney precursor cell into the metanephros.

(3) The kidney production method according to (1) or (2), in which the non-human animal is a pig.

(4) The kidney production method according to (1) or (2), in which the non-human animal is a mouse.

(5) A kidney produced by the production method according to any one of (1) to (4).

(6) A kidney including: a cell derived from a non-human animal; and a human cell, in which a proportion of the human cell is 70% by mass or more.

(7) A non-human animal including the kidney according to (5) or (6).

(8) An organ for transplantation, including: the kidney according to (5) or (6); a ureter; and a bladder.

(9) The organ for transplantation according to (8), in which the ureter and the bladder are derived from the non-human animal.

(10) A genetically modified non-human animal from which a metanephric mesenchyme of a metanephros can be tissue-specifically removed.

(11) The genetically modified non-human animal according to (10), from which an ureteric bud of the metanephros can be tissue-specifically removed.

(12) The genetically modified non-human animal according to (10) or (11), which is a genetically modified pig.

(13) A kit for kidney production, including: a metanephros of a non-human animal; a medicine which tissue-specifically removes a metanephric mesenchyme of the metanephros; and a human kidney precursor cell.

(14) The kit for kidney production according to (13), further including a medicine which tissue-specifically removes an ureteric bud of the metanephros.

(15) A medical drug for kidney regeneration, including: a metanephros of a non-human animal; a medicine which tissue-specifically removes a metanephric mesenchyme of the metanephros; and a human kidney precursor cell.

(16) The medical drug for kidney regeneration according to (15), further including a medicine which tissue-specifically removes an ureteric bud of the metanephros.

Advantageous Effects of Invention

According to the present invention, it is possible to provide a technique for producing a kidney from kidney precursor cells.

DESCRIPTION OF EMBODIMENTS

[Kidney Production Method]

Figure 1:
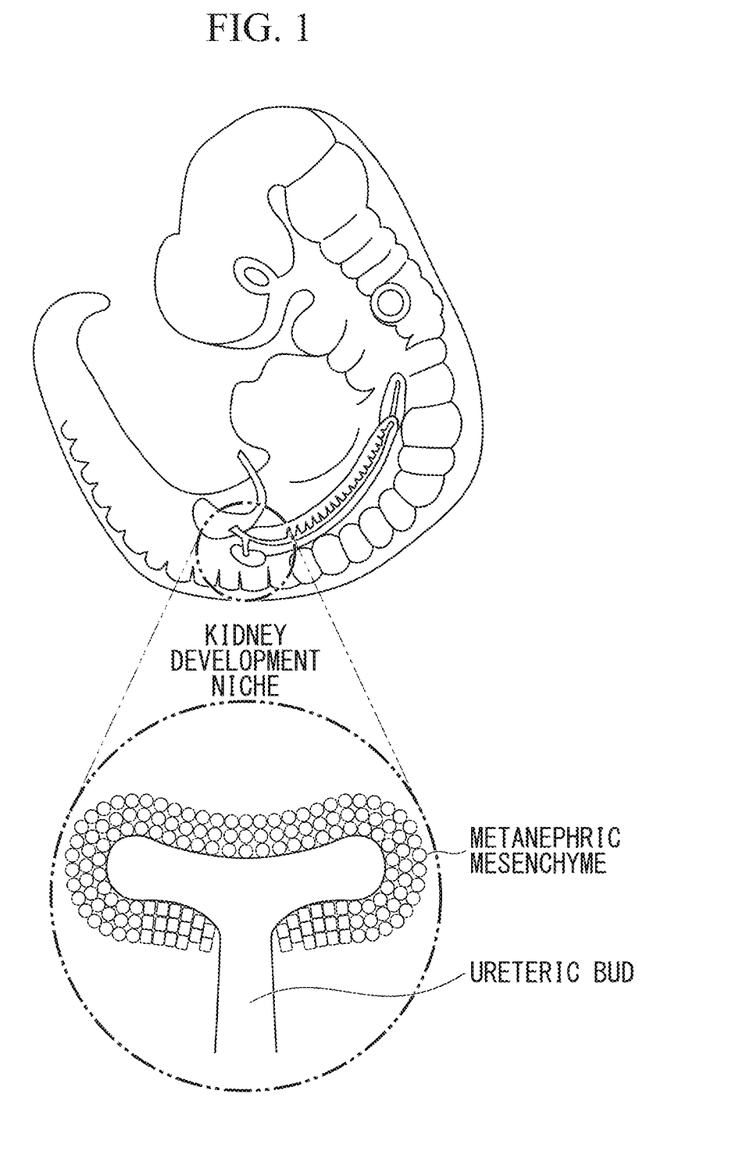
FIG. 1 is a schematic diagram showing a fetus of a mouse at around day 11 of embryonic development.

FIG. 1 is a schematic diagram showing a fetus of a mouse at around day 11 of embryonic development. A kidney is formed through three stages of pronephros, mesonephros, and metanephros. Among these, the pronephros and mesonephros are degenerated later. A kidney functioning in an adult body of mammals is the metanephros.

As shown in FIG. 1, the kidney is formed by an interaction between an ureteric bud and a metanephric mesenchyme surrounding the ureteric bud. The ureteric bud constitutes from collecting ducts to a ureter, and nephron precursor cells contained in the metanephric mesenchyme are the origin of glomeruli and kidney tubules. In the present specification, a kidney development region including the ureteric bud and the metanephric mesenchyme is called a kidney development niche.

In one embodiment, the present invention provides a kidney production method including a step (i) of tissue-specifically removing a metanephric mesenchyme of a metanephros of a non-human animal; a step (ii) of transplanting a human kidney precursor cell into the metanephros; and a step (iii) of advancing development of the metanephros, which is a step in which the transplanted human kidney precursor cell is differentiated and matured to form a part of the kidney.

In the related art, efficiency of a cell transplantation into a kidney development niche was extremely poor in terms of fixation. On the other hand, as described later in Examples, according to a production method of the present embodiment, transplanted kidney precursor cells can be engrafted with high efficiency. In addition, the transplanted kidney precursor cells take over a development program of a host and autonomously advance complicated differentiation induction to form a part of the kidney.

Figure 2A:
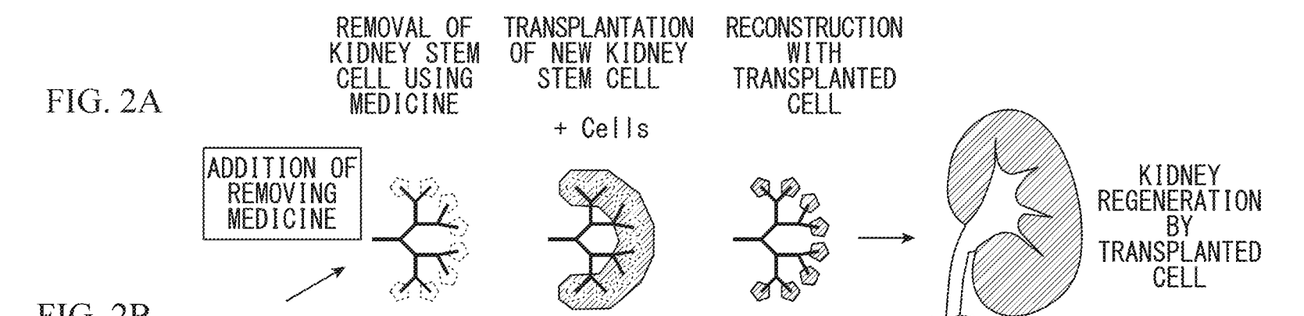
FIGS. 2A-C are schematic diagrams showing how a kidney is developed.
Figure 2B:
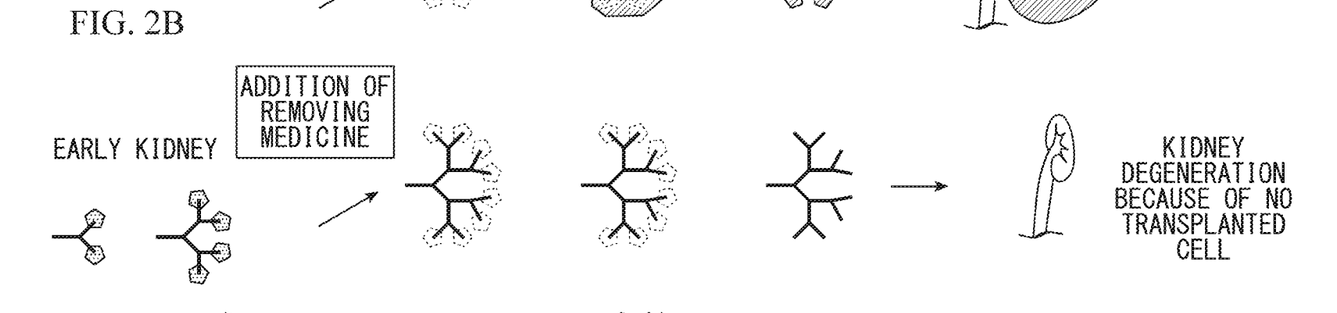
Figure 2C:
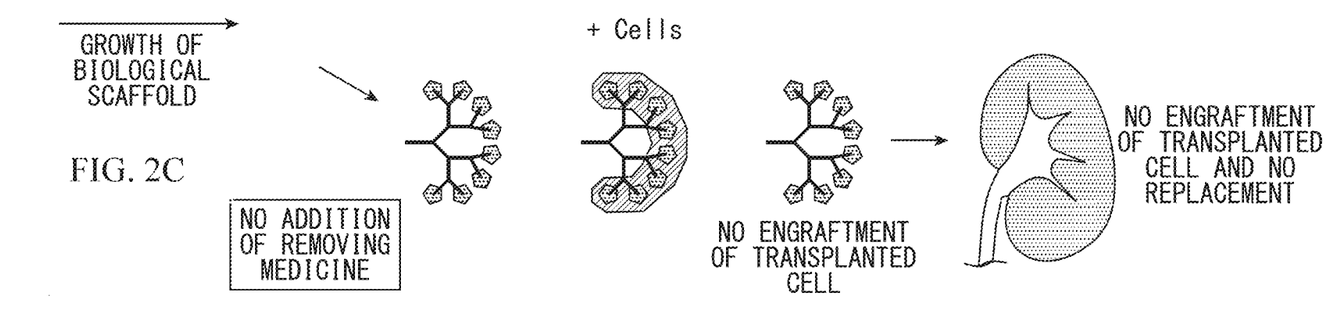

A kidney production method of the present embodiment will be described in more detail with reference to FIGS. 2A-2C. FIGS. 2A-2C are schematic diagrams showing how a kidney is developed. Among these, FIG. 2A corresponds to the kidney production method of the present embodiment.

In FIG. 2A, a metanephric mesenchyme of an early kidney of a non-human animal embryo is removed by adding a removing medicine. The addition results in a state in which kidney stem cells derived from the host do not exist, that is, a state in which the niche is empty. Subsequently, new human kidney precursor cells (kidney stem cells) are transplanted into this kidney development niche. Then, the transplanted human kidney precursor cells are fixed and take over the development program of the host to proceed the development of the kidney. As a result, the kidney is regenerated by the transplanted human kidney precursor cells.

Meanwhile, in FIG. 2B, a metanephric mesenchyme of an early kidney of a non-human animal embryo is removed by adding a removing medicine. The addition results in a state in which kidney stem cells derived from the host do not exist, that is, a state in which the niche is empty. In FIG. 2B, a transplantation of new human kidney precursor cells is not carried out. Even if the development of the kidney progresses in this state, the kidney will be degenerated.

In addition, in FIG. 2C, new human kidney precursor cells are transplanted into the metanephric mesenchyme of the early kidney of the non-human animal embryo while remaining the kidney stem cells derived from the host. However, competition by the existing cells derived from the host which occupies the kidney development niche is strong, and thus the transplanted human kidney precursor cells are not engrafted. As a result, a kidney composed of the cells derived from the host is formed.

Hereinafter, each step of the kidney production method of the present embodiment will be described in detail.

(Step (i))

In the present step, the metanephric mesenchyme of the non-human animal embryo is tissue-specifically removed. The non-human animal is not particularly limited, and may be, for example, a pig. Pigs are suitable for a transplantation into a human because of a size of organs thereof, and genetic modification techniques have also been established. Alternatively, the non-human animal may be a mouse. Mice are easy to use because genetic modification techniques and various experimental systems have been established.

Tissue-specific removal of the metanephric mesenchyme is not particularly limited as long as the metanephric mesenchyme can be tissue-specifically removed, and can be performed by using, for example, a genetic recombination technique.

A more specific method of tissue-specifically removing the metanephric mesenchyme will be described by using a mouse system as an example. Examples of the method of tissue-specific removal of the metanephric mesenchyme include a method in which an iDTR mouse expressing a diphteria toxin receptor (DTR) in a Cre recombinase activity-dependent manner is crossed with Six2-Cre mouse in which a Cre recombinase gene is introduced into downstream of a promoter of Six2; and the diphtheria toxin is brought into contact with the metanephros tissue of a progeny to be obtained.

The iDTR mouse has a transcription termination sequence flanked by two loxP sequences upstream of a gene encoding the diphtheria toxin receptor. For this reason, the diphtheria toxin receptor is not expressed in this state. However, if the transcription termination sequence flanked by the two loxP sequences is removed by the Cre recombinase, the diphtheria toxin receptor is expressed.

Since mice do not have the diphtheria toxin receptor, cells of mice are not killed even if the diphtheria toxin is brought into contact with the cells thereof. However, it is known that when the diphtheria toxin is brought into contact with cells of a mouse expressing the diphtheria toxin receptor, the cells are killed. In the above-described example, this phenomenon is utilized.

First, if the iDTR mouse is crossed with the Six2-Cre mouse specifically expressing the Cre recombinase in the metanephric mesenchyme, a mouse tissue-specifically expressing the diphtheria toxin receptor in the metanephros tissue among progenies to be obtained. Six2 is a transcription factor that is specifically expressed in the metanephric mesenchyme.

Subsequently, when the diphtheria toxin is brought into contact with the metanephros of the above-mentioned mouse, cells specifically in the metanephric mesenchyme are killed, and thus the metanephric mesenchyme can be tissue-specifically removed. That is, the kidney development niche can be emptied.

The contact with the diphtheria toxin may be carried out by injecting the diphtheria toxin into a parent mouse or a fetus of a mouse. Alternatively, the contact may be carried out by extracting the metanephros from a fetus of a mouse, organ-culturing the extracted metanephros, adding the diphtheria toxin to a medium, and the like. Alternatively, the contact may be carried out by transplanting the extracted metanephros into a para-aortic region or greater omentum of a patient, locally administering the diphtheria toxin into a body of the patient, and the like.

The above-described method is one of methods of tissue-specifically removing the metanephric mesenchyme, and can be applied to not only mice but also any non-human animal.

(Step (ii))

Subsequently, in the present step, the human kidney precursor cells are transplanted into the metanephros. The step (i) and step (ii) may be carried out in parallel. That is, a time of emptying the niche and a time of transplanting the human kidney precursor cells may overlap. For example, the addition of the removing medicine and the transplantation of the human kidney precursor cells may be carried out at the same time.

Examples of the human kidney precursor cells include kidney precursor cells (kidney stem cells) differentiation-induced from pluripotent stem cells such as mesenchymal stem cells (MSCs), iPS cells, and ES cells derived from humans. The human kidney precursor cells may be cells derived from a patient or allogeneic cells whose rejection reaction is suppressed in a patient.

It is preferable that the human kidney precursor cells be cells derived from a patient that is a subject of the transplantation of the kidney after production. Examples of the kidney precursor cells differentiation-induced from mesenchymal stem cells sorted from human bone marrow, adipose tissue, bloodshed, or umbilical cord blood. The kidney precursor cells may be kidney precursor cells differentiation-induced from mesenchymal stem cells sorted from bone marrow, bloodshed, or umbilical cord blood of a patient himself. A sorting method may be a method according to general surgical medical techniques. It is preferable that the sorted cells be cultivated for 2 to 5 times by selecting optimum conditions. In addition, the cultivation may be carried out by using a medium kit exclusive for human mesenchymal stem cells manufactured by Cambrex BioScience, or the like for the purpose of continuing the cultivation while suppressing the transformation of the mesenchymal stem cells.

If desired, a desired gene may be introduced into the human kidney precursor cells using adenovirus, retrovirus, or the like. For example, the gene may be introduced so as to express glial cell line-derived neurotrophic factor-GDNF for the purpose of assisting kidney formation. This is because the mesenchymal tissue immediately before the kidney is formed becomes to express GDNF, and the ureteric bud expressing c-ret which is a receptor thereof is drawn, thereby completing a first important step of the kidney development.

As a method of transplantation, for example, the human kidney precursor cells may be injected into the metanephros using an injection needle or the like. The number of human kidney precursor cells to be transplanted is preferably about $1 \times 10^3$ to $1 \times 10^6$, for example. Because the transplantation of the human kidney precursor cells can be performed in vitro, skill for the operation is not required, and the operation is easily performed.

As a result of transplanting the human kidney precursor cells, the kidney to be produced is composed of human cells transplanted into the kidney development niche. This kidney can be transplanted into a patient so as to function. The kidney precursor cells are more preferably cells in which the rejection reaction with cells of the patient himself or the patient is suppressed.

(Step (iii))

Subsequently, in the present step, the development of the metanephros after transplanting the human kidney precursor cells progresses. As a result, the transplanted human kidney precursor cells are differentiated and matured, thereby forming a part of the kidney. In a case where the human kidney precursor cells are transplanted without extracting the metanephros from the embryo, the progression of the metanephros can be carried out by returning the embryo back to the uterus of the parent animal, performing whole embryo culture, and the like. Alternatively, in a case where the metanephros is extracted to transplant the human kidney precursor cells, the progression can be carried out by continuing an organ culture of the metanephros. Alternatively, in a case where the metanephros is transplanted into the para-aortic region or greater omentum of the patient and the human kidney precursor cells are transplanted into the metanephros in the body of the patient, the progression of the development of the metanephros can be carried out by let the metanephros grow at that site.

As a result, as will be described later in Examples, the transplanted human kidney precursor cells take over the developmental program of the host, autonomously advance complicated differentiation induction while interacting with the remaining ureteric bud, and thereby forming the glomeruli and kidney tubules. In addition, in order to completely remove the kidney precursor cells constituting the metanephric mesenchyme on the host side, the glomeruli and kidney tubules to be regenerated are composed only of cells derived from substantially the transplanted human kidney precursor cells.

The term "substantially" means that in a case where the kidney is produced using the kidney development niche of the non-human animal, mixing of cells other than the transplanted human kidney precursor cells is not excluded. In other words, it is preferable that 70% by mass or more of the glomeruli and kidney tubules to be regenerated be composed of the transplanted human kidney precursor cells, it is more preferable that 80% by mass or more of the glomerulus and kidney tubules to be regenerated be composed of the transplanted human kidney precursor cells, it is even more preferable that 90% by mass or more of the glomeruli and kidney tubules to be regenerated be composed of the transplanted human kidney precursor cells, it is still more preferable that 95% by mass or more of the glomeruli and kidney tubules to be regenerated be composed of the transplanted human kidney precursor cells, and it is particularly preferable that 99% by mass or more of the glomerulus and kidney tubules to be regenerated be composed of the transplanted human kidney precursor cells.

The kidney production method of the present embodiment may further include a step (iv) of tissue-specifically removing an ureteric bud of the metanephros; and a step (v) of transplanting a human kidney precursor cell into the metanephros. In addition, the steps (iv) and (v) may be performed before the steps (i) to (iii) described above, or may be performed after the steps (i) to (iii) described above. Furthermore, the step (iii) may further be carried out after the steps (iv) and (v).

As a result, not only the metanephric mesenchyme but also the ureteric bud can be replaced with cells derived from the transplanted human kidney precursor cells. As a result, it is possible to produce the kidney substantially consisting only of the cells derived from the transplanted human kidney precursor cells. Hereinafter, each step will be described.

(Step (iv))

In the present step, the ureteric bud of the metanephros of the non-human animal is tissue-specifically removed. The tissue-specific removal of the ureteric bud is not particularly limited as long as the ureteric bud can be tissue-specifically removed, and can be performed by using, for example, a genetic recombination technique.

For example, it is possible to use a mouse obtained by further introducing a gene encoding a Cre-ER protein into downstream of an ureteric bud-specific promoter in the mouse obtained by crossing the iDTR mouse and the Six2-Cre mouse described above. Examples of the ureteric bud-specific promoter include a promoter of cytokeratin 8, a promoter of HoxB7, and the like.

Examples of such a mouse include an iDTR mouse having a genotype of Six2-Cre$^{tg/wt}$ cytokeratin 8-Cre-ER$^{tg/wt}$, an iDTR mouse having a genotype of Six2-Cre$^{tg/wt}$ HoxB7-Cre-ER$^{tg/wt}$, and the like. The term "tg" represents that the type is transgenic, and "wt" represents a wild type.

The Cre-ER protein is a fusion protein of a Cre recombinase and a mutant estrogen receptor. The above-described mouse expresses Cre-ER in a promoter-dependent manner with respect to cytokeratin 8 or HoxB7, which is a marker for the ureteric bud.

Although the Cre-ER protein is generally present in the cytoplasm, the Cre-ER protein is translocated into the nucleus by binding with tamoxifen, which is an estrogen derivative, and recombines against the loxP sequence. By utilizing the above description, It is possible to tamoxifen-dependently adjust a working time of a Cre-loxP system. Therefore, even if Cre-ER and Cre are expressed at the same time, it is possible to control the expression of Cre-ER activity depending on whether tamoxifen is administered or not. Cre-ERT, Cre-ERT2, or the like, which is a modified form of Cre-ER, may be used instead of Cre-ER.

The mouse described above expresses the diphtheria toxin receptor specifically in the metanephric mesenchyme. In this case, it is preferable to first perform the steps (i), (ii), and (iii) described above. Specifically, the metanephric mesenchyme is removed by bringing the diphtheria toxin into contact with the metanephros of the mouse embryo. Subsequently, the human kidney precursor cells are transplanted into the metanephros by the above-described method so that the development of the metanephros progresses. As a result, the metanephric mesenchyme is regenerated by the transplanted human kidney precursor cells.

Subsequently, when tamoxifen is brought into contact with this metanephros, the diphtheria toxin receptor is expressed specifically in the ureteric bud. In this case, by bringing the diphtheria toxin into contact with this metanephros, the ureteric bud can be tissue-specifically removed. That is, the kidney development niche can be emptied.

In the above example of the mouse, the gene encoding the Cre protein is introduced into downstream of the metanephric mesenchyme-specific promoter, and the gene encoding the Cre-ER protein is introduced into downstream of the ureteric bud-specific promoter. However, the gene encoding the Cre-ER protein may be introduced into downstream of the metanephric mesenchyme-specific promoter, and the gene encoding the Cre protein may be introduced into downstream of the ureteric bud-specific promoter. In addition, Cre-ERT, Cre-ERT2, or the like, which is a modified form of Cre-ER, may be used instead of Cre-ER.

For example, a mouse obtained by further introducing the gene encoding the Cre protein into downstream of the ureteric bud-specific promoter in the mouse obtained by crossing the iDTR mouse with the mouse in which the gene encoding the Cre-ER protein is introduced into downstream of the metanephric mesenchyme-specific promoter, may be used.

More specific examples of the mouse include an iDTR mouse having a genotype of Six2-Cre-ER$^{tg/wt}$HoxB7-Cre$^{tg/wt}$, and the like. The terms "tg" and "wt" have the same meanings as those described above.

This mouse expresses Cre-ER specifically in the metanephric mesenchyme. In addition, the diphtheria toxin receptor is specifically expressed in the ureteric bud. Therefore, in the case of using this mouse, the steps (iv) and (v) are carried out before carrying out the steps (i) to (iii). Specifically, by bringing the diphtheria toxin into contact with the metanephros of the mouse embryo, the ureteric bud can be removed.

The above-described method is one of methods of tissue-specifically removing the ureteric bud, and can be applied to not only mice but also any non-human animal.

(Step (v))

Subsequently, in the present step, the human kidney precursor cells are transplanted into the metanephros so that the development of the ureteric bud progresses. As a result, the ureteric bud is regenerated by the transplanted human kidney precursor cells. The step (iv) and step (v) may be carried out in parallel. That is, a time of emptying the niche and a time of transplanting the human kidney precursor cells may overlap. For example, the addition of the removing medicine and the transplantation of the human kidney precursor cells may be carried out at the same time.

Subsequently, the above-described step (iii) is carried out so that the development of embryos (metanephros) transplanted with the human kidney precursor cells progresses. As a result, the transplanted human kidney precursor cells are differentiated and matured, thereby forming a part of the kidney.

As the human kidney precursor cells, cells that are the same as those described above can be used. In a case where the human kidney precursor cells have the same origin as the human kidney precursor cells in the regeneration of the metanephric mesenchyme described above, not only the glomeruli and kidney tubules but also the collecting ducts and ureter are composed of cells of the same origin in the kidney to be produced.

Therefore, if the human kidney precursor cells are cells derived from the patient or cells in which the rejection reaction with the patient is suppressed, it is possible to produce the kidney with less rejection reaction in a case of transplanting these kidney precursor cells into the patient.

For example, in a case where the steps (iv) and (v) are performed first using the iDTR mouse having the genotype of Six2-Cre-ER$^{tg/wt}$HoxB7-Cre$^{tg/wt}$, the steps (i), (ii), and (iii) described above may be subsequently carried out. That is, when tamoxifen is brought into contact with the metanephros of the mouse whose ureteric bud has been regenerated by transplanted human kidney precursor cells, the diphtheria toxin receptor is expressed specifically in the metanephric mesenchyme in this case. In this case, by bringing the diphtheria toxin into contact with this metanephros, the metanephric mesenchyme can be tissue-specifically removed. That is, the kidney development niche can be emptied.

In the kidney production method of the present embodiment, any of the removal of the metanephric mesenchyme and the removal of the ureteric bud may be performed first. In a case of removing the ureteric bud first, the above-described Cre-loxP system may be appropriately modified.

[Kidney]

In one embodiment, the present invention provides a kidney produced by the production method described above. The kidney of the present embodiment is produced from desired human kidney precursor cells by utilizing the kidney development niche and the developmental program of a host non-human animal. Therefore, the kidney can be transplanted into the patient so as to function.

As described above, the kidney of the present embodiment is formed by replacing the metanephric mesenchyme or the ureteric bud, or both thereof with the transplanted human kidney precursor cells. For this reason, in particular, in a case of the kidney in which both metanephric mesenchyme and ureteric bud are replaced with the transplanted human kidney precursor cells, this kidney is substantially composed only of cells derived from the transplanted human kidney precursor cells. For this reason, merely by specifying the cells constituting the kidney, it is difficult to specify whether a kidney is the kidney produced by the above-described production method, or is a kidney of a patient from which the transplanted human kidney precursor cells had been prepared.

The kidney includes cells derived from a non-human animal and human cells, in which a proportion of the human cells is 70% by mass or more, more preferably 80% by mass or more, even more preferably 90% by mass or more, still more preferably 95% by mass or more, and particularly preferably 99% by mass or more. Examples of the non-human animals include pigs, mice, and the like as described above. Such a kidney can be produced by the above-described kidney production method.

The kidney of the present embodiment may be formed by replacing the human kidney precursor cells, which are transplanted with the metanephric mesenchyme by the above-described production method, for example. In this case, the collecting ducts and ureter derived from the ureteric bud are derived from a host non-human animal.

Alternatively, the kidney of the present embodiment may be formed by replacing the human kidney precursor cells, which are transplanted with the ureteric bud by the above-described production method. In this case, the glomeruli and kidney tubules derived from the metanephric mesenchyme are derived from a host non-human animal.

Alternatively, the kidney of the present embodiment may be formed by replacing the human kidney precursor cells, which are transplanted with both metanephric mesenchyme and ureteric bud by the above-described production method. In this case, the kidney is a kidney derived from the human kidney precursor cells, to which substantially all of the glomeruli, kidney tubules, collecting ducts, and ureter are transplanted. However, cells derived from a host non-human animal may remain in the formed kidney in some cases.

[Organ for Transplantation]

In one embodiment, the present invention provides an organ for transplantation including any of the kidney, ureter, and bladder described above.

The inventors of the present invention have previously been able to generate urine by transplantation of regenerated kidneys. However, the inventors have found that generated urine could not be excreted, which resulted in hydronephrosis, and therefore kidney functions could not be maintained for a long time. The inventors of the present invention also have found that, by transplanting a structure including not only the kidney but also the kidney, the ureter, and the bladder, not only generation of urine but also excretion of the generated urine is possible.

Therefore, since the organ for transplantation of the present embodiment includes the kidney, the ureter, and the bladder, even in a case where this organ is transplanted to a patient, not only generation of urine but also excretion of the generated urine is possible, and kidney functions can be maintained for a long time.

The organ for transplantation of the present embodiment may be transplanted into the para-aortic region or greater omentum of the patient, and may be transplanted into, for example, the spleen (around the splenic artery) of the patient. In addition, the bladder constituting the organ for transplantation described above may be connected to the ureter of the patient. In this manner, an organ structure in which the kidney, a first ureter, a first bladder, a second ureter, and a second bladder are connected in this order is formed. The second ureter and the second bladder are the ureter and bladder that the patient has inherently.

By forming such an organ structure, excretion of the urine generated by the regenerated kidneys constituting the above-described organ for transplantation becomes easier.

In the organ for transplantation of the present embodiment, the ureter (first ureter) and the bladder (first bladder) may be derived from the non-human animal in the kidney production method described above. Because the ureter and bladder generally have low immunogenicity, a problem is less likely to occur even if the ureter and the bladder are derived from the non-human animal. The non-human animal is a host animal which provides the kidney development niche serving as a scaffold in the kidney production method described above. That is, the organ for transplantation of the present embodiment may be composed of the kidney formed by the above-described production method, a ureter, and a bladder.

The organ for transplantation of the present embodiment can be extracted from a non-human animal, stored, and distributed while being in a state where the kidney, ureter, and bladder are connected to each other. The organ for transplantation may be frozen for storage and distribution. Alternatively, the organ for transplantation of the present embodiment can be distributed in a form of a non-human animal having the organ for transplantation of the present embodiment.

[Genetically Modified Non-Human Animal]

In one embodiment, the present invention provides a genetically modified non-human animal from which a metanephric mesenchyme of a metanephros can be tissue-specifically removed. The genetically modified non-human animal may be, for example, a genetically modified mouse or a genetically modified pig. In addition, a genetic modification method is not particularly limited, and may be a method using ES cells or a method using genome editing.

By carrying out the above-mentioned kidney production method using the genetically modified non-human animal of the present embodiment, the kidney capable of being transplanted into a human so as to function can be produced. Therefore, the genetically modified non-human animal of the present embodiment can be said to be used for producing the kidney described above. Alternatively, the genetically modified non-human animal of the present embodiment can be said to be used for producing the organ for transplantation described above.

More specific examples of the genetically modified non-human animal of the present embodiment include a genetically modified non-human animal that has a construct expressing a diphtheria toxin receptor (DTR) in a Cre recombinase activity-dependent manner as described above, and a construct in which a Cre recombinase gene is connected downstream of the metanephric mesenchyme-specific promoter. This system can be applied to non-human animals which are not originally sensitive to the diphtheria toxin. Examples of such a non-human animal include a mouse.

Examples of the metanephric mesenchyme-specific promoter include a promoter of Six2 which is a transcription factor, and the like. This genetically modified non-human animal expresses Cre recombinase specifically in the metanephric mesenchyme. As a result, the diphtheria toxin receptor is expressed specifically in the metanephric mesenchyme. In this case, when the diphtheria toxin is brought into contact with the metanephros, the metanephric mesenchyme can be specifically killed and removed.

As Cre recombinase, Cre-ER capable of translocating Cre recombinase into the nucleus in the presence of tamoxifen, and the like may be used. In this case, Cre recombinase can be translocated into the nucleus to express the diphtheria toxin receptor only in a case where tamoxifen is administered.

Examples of the genetically modified non-human animal of the present embodiment further include a genetically modified non-human animal that has a construct expressing diphtheria toxin (diphteria toxin A subunit: DT-A) in a Cre recombinase activity-dependent manner, and a construct in which a Cre recombinase gene is connected downstream of the metanephric mesenchyme-specific promoter. This system can be applied to non-human animals which are originally sensitive to the diphtheria toxin. Examples of such a non-human animal include a pig.

Examples of the metanephric mesenchyme-specific promoter include a promoter of Six2 which is a transcription factor, and the like. This genetically modified non-human animal expresses Cre recombinase specifically in the metanephric mesenchyme. As a result, diphtheria toxin can be specifically expressed in the metanephric mesenchyme so as to be killed and removed.

As Cre recombinase, Cre-ER capable of translocating Cre recombinase into the nucleus in the presence of tamoxifen, and the like may be used. In this case, Cre recombinase can be translocated into the nucleus to express the diphtheria toxin only in a case where tamoxifen is administered. In addition, Cre-ERT, Cre-ERT2, or the like, which is a modified form of Cre-ER, may be used instead of Cre-ER.

The non-human animal of the present embodiment may further be genetically modified so that the ureteric bud of the metanephros can be tissue-specifically removed. Specific examples thereof include a genetically modified non-human animal which further has a construct in which the Cre recombinase gene is connected downstream of the ureteric bud-specific promoter, in addition to the construct expressing the diphtheria toxin receptor (DTR) in the Cre recombinase activity-dependent manner, and the construct in which the Cre recombinase gene is connected downstream of the metanephric mesenchyme-specific promoter. This system can be applied to non-human animals which are not originally sensitive to the diphtheria toxin. Examples of such a non-human animal include a mouse.

Examples of the ureteric bud-specific promoter include a promoter of cytokeratin 8, a promoter of HoxB7, and the like. This genetically modified non-human animal expresses Cre recombinase specifically in the ureteric bud. As a result, the diphtheria toxin receptor is specifically expressed in the ureteric bud. In this case, when the diphtheria toxin is brought into contact with the metanephros, the ureteric bud can be specifically killed and removed. As the Cre recombinase, Cre-ER, Cre-ERT, Cre-ERT2, and the like may be used.

In addition, in the genetically modified non-human animal of the present embodiment, a system for killing cells can be used without particular limitation as long as the system can be applied to a target non-human animal species and can be operated in a tissue-specific manner or in a time-specific manner.

Therefore, a configuration in which the cells are killed by a system other than the diphtheria toxin or diphtheria toxin receptor may be adopted. Examples thereof include a system that expresses a herpes simplex virus-derived thymidine kinase gene (HSV-TK) which induces apoptosis by administration of ganciclovir, at downstream of the tissue-specific promoter. In cells expressing HSV-TK, cell death is induced under administration of ganciclovir.

Alternatively, a system that induces apoptosis by dimerizing Caspase-3, Caspase-8, Caspase-9, and the like by administration of AP20187 may be used.

The genetically modified non-human animal of the present embodiment is not limited to the method described above as long as the metanephric mesenchyme or the ureteric bud of the metanephros can be tissue-specifically removed, and may have various genetic recombination systems and a combination of genetic recombination systems.

[Kit for Kidney Production]

In one embodiment, the present invention provides a kit for kidney production including a metanephros of a non-human animal; a medicine that tissue-specifically removes a metanephric mesenchyme of the embryo; and a human kidney precursor cell.

By carrying out the above-mentioned kidney production method using the kit of the present embodiment, the kidney can be produced. Examples of the non-human animals include pigs, mice, and the like as described above. The metanephros of the non-human animal may be provided in a form of an embryo or may be provided in a form of a parent animal including a fetus. In addition, the metanephros may be in a state of being connected to a cloaca which later becomes the bladder. In this case, the metanephros forms the kidney and ureter, the cloaca forms the bladder, and therefore a state in which the kidney, ureter, and bladder are connected is formed. As a result, as described above, the produced kidney is capable of not only generating urine but also excreting the produced urine.

In the kit of the present embodiment, examples of the medicine that tissue-specifically removes the metanephric mesenchyme include the above-mentioned diphtheria toxin, and the like. In this case, examples of a non-human animal include a non-human animal that expresses the diphtheria toxin receptor specifically in the metanephric mesenchyme by the Cre-loxP system or the like.

Alternatively, various conditional knockout systems other than those described above can also be used as long as the metanephric mesenchyme can be tissue-specifically removed thereby. As the medicine for tissue-specifically removing the metanephric mesenchyme, diphtheria toxin (iDTR system), tamoxifen (Cre-ERT2 system), tacrolimus (Mos-iCsp3 system), doxycycline, tetracycline (Tet-On/off system), ganciclovir (herpes virus-derived thymidine kinase gene system), and the like can be used depending on a system to be used.

These conditional knockout systems can be produced using genome editing techniques and the like, and can tissue-specifically remove cells in the kidney development niche of the non-human animal. In addition, a time at which cells are removed can be controlled by administering the medicine. By using these systems, it is possible to spatiotemporal-specifically control the removal of target cells and construct a living scaffold suitable for the kidney regeneration.

A method for administering the medicine that tissue-specifically removes the metanephric mesenchyme is not particularly limited, and may be appropriately selected according to the medicine to be used. Examples thereof include addition to a medium such as organ culture in vitro, local administration in vivo, intraperitoneal administration, intravenous injection, oral administration, and the like.

In addition, examples of the human kidney precursor cell include a kidney precursor cell derived from a patient, and the like. Examples of the human kidney precursor cell include kidney precursor cells differentiation-induced from iPS cells, mesenchymal stem cells (MSCs), and the like which are derived from a patient; kidney precursor cells differentiation-induced from pluripotent stem cells such as allogeneic iPS cells or ES cells, in which the rejection reaction in a patient is suppressed; and the like. The allogeneic iPS cells described above can be obtained from, for example, an iPS cell bank.

The kidney production may be performed outside the body of the patient, and then the kidney may be transplanted into the para-aortic region or greater omentum of the patient. Alternatively, the kidney production may be performed in the body of the patient. More specifically, the kidney may be produced by transplanting the metanephros of the non-human animal into the para-aortic region or greater omentum of the patient first, emptying the niche of the metanephros in the body of the patient, and transplanting the human kidney precursor cells. This method is advantageous in that a vascular system drawn into the regenerated kidney becomes a blood vessel of the patient, and that a functional kidney can be constructed.

The kit of the present embodiment may further include a medicine that tissue-specifically removes the ureteric bud of the metanephros. Accordingly, it is possible to produce a kidney derived from the human kidney precursor cells transplanted with not only tissues derived from the metanephric mesenchyme but also tissues derived from the ureteric bud.

Examples of the medicine that tissue-specifically removes the ureteric bud include a combination of tamoxifen and diphtheria toxin as described above, and the like. In this case, examples of a non-human animal include a non-human animal that expresses the diphtheria toxin receptor specifically in the metanephric mesenchyme by the Cre-loxP system or the like, and also expresses the diphtheria toxin receptor specifically in the ureteric bud by administration of tamoxifen.

Alternatively, any of the various conditional knockout systems described above can be used to remove the ureteric bud. In this case, the medicine that tissue-specifically removes the ureteric bud becomes an appropriate medicine according to an adopted system.

By combining the above-described various conditional knockout systems, it is possible to remove a plurality of target tissues at any timing. For example, after tissue-specifically removing the ureteric bud by using tamoxifen, the metanephric mesenchyme can be tissue-specifically removed by using tacrolimus in a stepwise manner. As a result, almost all of the kidney tissues can be tissues derived from the transplanted human kidney precursor cells.

[Medical Drug for Kidney Regeneration]

In one embodiment, the present invention provides a medical drug for kidney regeneration including a metanephros of a non-human animal; a medicine that tissue-specifically removes a metanephric mesenchyme of the metanephros; and a human kidney precursor cell.

According to the medical drug of the present embodiment, it is possible to perform the regeneration of the kidney within the body of the patient as described above.

The medical drug of the present embodiment can be used as follows. First, the metanephros of a non-human animal is transplanted into the para-aortic region or greater omentum of the patient. As the metanephros of the non-human animal, the same metanephros as in the above-described kit for kidney production can be used.

Subsequently, the medicine that tissue-specifically removes the metanephric mesenchyme is administered to the patient. As the medicine, the same medicine as in the above-described kit for kidney production can be used. It is preferable that the administration of the medicine be appropriately carried out by local administration, intraperitoneal administration, intravenous injection, oral administration, and the like depending on the medicine to be used.

Subsequently, the human kidney precursor cells are transplanted. Examples of the human kidney precursor cell include kidney precursor cells differentiation-induced from iPS cells, mesenchymal stem cells (MSCs), and the like which are derived from a patient; kidney precursor cells differentiation-induced from allogeneic iPS cells or ES cells, in which the rejection reaction in a patient is suppressed; and the like. Thereafter, the development of the transplanted metanephros progresses, thereby producing (regenerating) the kidney composed of the human kidney precursor cells transplanted in the body of the patient.

This medical drug of the present embodiment is advantageous in that a vascular system drawn into the regenerated kidney becomes a blood vessel of the patient, and that a functional kidney can be constructed.

The medical drug for kidney regeneration may further include a medicine that tissue-specifically removes the ureteric bud of the metanephros. Accordingly, it is possible to regenerate a kidney derived from the human kidney precursor cells transplanted with not only tissues derived from the metanephric mesenchyme but also tissues derived from the ureteric bud. As the medicine that tissue-specifically removes the ureteric bud of the metanephros, the same medicine as in the above-described kit for kidney production can be used.

OTHER EMBODIMENTS

In one embodiment, the present invention provides a kidney transplantation method including: a step (a) of transplanting the organ for transplantation which has the kidney, ureter, and bladder described above into a body of a patient; and a step (b) of connecting a bladder of the organ for transplantation to a ureter of the patient at a predetermined time after the transplantation.

The method of the present embodiment can also be said to be a method for treating a kidney disease. As the organ for transplantation, those described above can be used.

By allowing the organ for transplantation which is transplanted in the step (a) to stand for a predetermined period, the organ for transplantation grows, and urine production is started. The predetermined period may refer to any period up to the organ for transplantation sufficiently grows, but before occurrence of hydronephrosis. The predetermined period may be appropriately adjusted depending on the symptoms and the like of the patient, but may be, for example, 1 to 10 weeks.

Subsequently, the step (b) is performed at a predetermined period of time (after 1 to 10 weeks) after transplantation. In the step (b), the bladder of the organ for transplantation and the ureter of the patient are connected. The ureter of the patient is connected to the bladder of the patient.

By connecting the bladder of the organ for transplantation and the bladder of the patient with the ureter of the patient, the urine produced by the organ for transplantation can be excreted to the bladder of the patient. More specifically, the urine produced by the kidney of the organ for transplantation is excreted to the bladder of the organ for transplantation through the ureter of the organ for transplantation, and then is excreted to the bladder of the patient from the bladder of the organ for transplantation through the ureter of the patient.

By the method of the present embodiment, the urine produced by the kidney of the organ for transplantation can be excreted to the bladder of the patient.

In one embodiment, the present invention provides a method for treating a kidney disease, including a step (a1) of transplanting a metanephros and a cloaca of a non-human animal into a body of a patient; a step (a2) of tissue-specifically removing a metanephric mesenchyme of a metanephros; a step (a3) of transplanting a human kidney precursor cell into the metanephros, which is a step in which the transplanted human kidney precursor cell is differentiated and matured to form a part of the kidney, and the cloaca is differentiated and matured to form a bladder so as to connect the bladder to the kidney via a ureter; and a step (b) of connecting the bladder to a ureter of the patient at a predetermined time after the transplantation of the human kidney precursor cell.

In the method of the present embodiment, the production (regeneration) of the kidney is performed in the body of the patient. The step (a2) and the step (a3) may be carried out in parallel. That is, a time of emptying the niche and a time of transplanting the human kidney precursor cells may overlap. For example, the addition of the removing medicine and the transplantation of the human kidney precursor cells may be carried out at the same time.

When a predetermined period has elapsed from the transplantation of the human kidney precursor cells in the step (a3), the transplanted human kidney precursor cells form the kidney, and urine production is started. The predetermined period may refer to any period up to the kidney and bladder sufficiently grow, but before occurrence of hydronephrosis. The predetermined period may be appropriately adjusted depending on the symptoms and the like of the patient, but may be, for example, 2 to 4 weeks.

Subsequently, the step (b) is performed at a predetermined period of time (after 2 to 4 weeks) after transplantation. In the step (b), the bladder formed by differentiation and maturation of the cloaca is connected to the ureter of the patient. The ureter of the patient is connected to the bladder of the patient.

The treatment method of the present embodiment may further include a step (a2') in which the ureteric bud of the metanephros is tissue-specifically removed. Accordingly, not only the metanephric mesenchyme but also the ureteric bud can be replaced with cells derived from the transplanted human kidney precursor cells. As a result, it is possible to produce the kidney substantially consisting only of the cells derived from the transplanted human kidney precursor cells.

In a case of carrying out the step (a2'), any of the step (a2) and the step (a2') may be carried out first, but after carrying out either one step thereof, it is preferable to provide a period of 4 to 7 days before carrying out the other step. Between the steps, transplanted human kidney precursor cells progress the development program to be differentiated.

The step (a2) and step (a3), or the step (a2') and step (a3) may be carried out in parallel. That is, a time of emptying the niche and a time of transplanting the human kidney precursor cells may overlap. For example, the addition of the removing medicine and the transplantation of the human kidney precursor cells may be carried out at the same time.

For example, the step (a2) and step (a3) may be carried out at the same time first, and after a predetermined period, the step (a2') and step (a3) may be carried out at the same time. Alternatively, the step (a2') and step (a3) may be carried out at the same time first, and after a predetermined period, the step (a2) and step (a3) may be carried out at the same time.

EXAMPLES

Next, the present invention will be described in more detail by showing experimental examples, but the present invention is not limited to the following experimental examples.

Experimental Example 1

(Tissue-Specific Removal of Metanephric Mesenchyme in Mouse Embryo) The iDTR mouse expressing the diphtheria toxin receptor (DTR) in the Cre recombinase activity-dependent manner was crossed with the Six2-Cre mouse in which the Cre recombinase gene was introduced into downstream of a promoter of Six2. Six2 is a transcription factor that is specifically expressed in the metanephric mesenchyme.

Subsequently, a mouse that expressed the diphtheria toxin receptor specifically in the metanephric mesenchyme was selected from an $F_1$ mouse on embryonic day 13, and the metanephros was extracted. The extracted metanephros was organ-cultured according to a standard method, and diphtheria toxin was added to the medium. As a result, Six2-positive kidney precursor cells of the metanephric mesenchyme, in which the diphtheria toxin receptor was expressed were killed. As a result, the metanephric mesenchyme was tissue-specifically removed.

Experimental Example 2

(Transplantation of Kidney Precursor Cells)
The kidney precursor cells derived from a wild-type mouse were prepared from the metanephros by a standard method and dissociated into single cells using a cell dissociation reagent. Subsequently, $1 \times 10^5$ kidney precursor cells were transplanted into metanephros tissue from which the metanephric mesenchyme was tissue-specifically removed, which was prepared in Experimental Example 1. Thereafter, the organ culture of the metanephros tissue was continued.

Experimental Example 3

Figure 3:
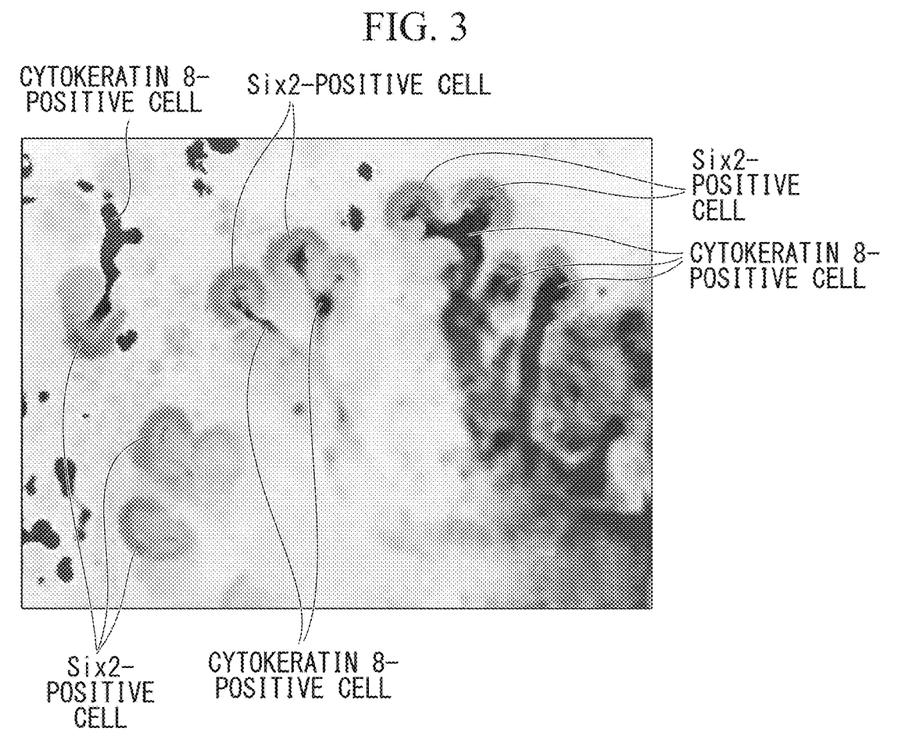
FIG. 3 is a photograph showing a result of immunostaining of a kidney tissue sample in Experimental Example 3.

(Immunostaining 1 of Kidney Tissue)
The metanephros tissue of Experimental Example 2 was fixed with 4% paraformaldehyde after being cultured for 5 days from the transplantation of the kidney precursor cells, and therefore a tissue section sample was prepared. Subsequently, Six2 which is a marker of the metanephric mesenchyme and cytokeratin 8 which is a marker of the ureteric bud were immunostained, respectively. FIG. 3 is a fluorescence microscopy photograph showing the result of immunostaining. The magnification is 100 times. In FIG. 3, Six 2-positive cells are derived from the transplanted kidney precursor cells. In addition, cytokeratin 8-positive cells are derived from the host animal ($F_1$ mouse of Experimental Example 1).

As a result, it was confirmed that, using the ureteric bud derived from the $F_1$ mouse of Experimental Example 1 as a scaffold, the kidney precursor cells transplanted in Experimental Example 2 took over the development program of the host, autonomously advanced complicated differentiation induction, and thus formed the metanephric mesenchyme. This result shows that the cells constituting the metanephric mesenchyme can be replaced with the cells derived from the transplanted kidney precursor cells by the above-described method.

Experimental Example 4

(Immunostaining 2 of Kidney Tissue)

The kidney precursor cells derived from a transgenic mouse (GFP tg mouse) into which a green fluorescent protein (GFP) gene was introduced were prepared from the metanephros by a standard method and dissociated into single cells using a cell dissociation reagent. Subsequently, $1 \times 10^5$ kidney precursor cells were transplanted into metanephros tissue from which the metanephric mesenchyme was tissue-specifically removed, which was prepared in the same manner as in Experimental Example 1. Thereafter, the organ culture of the metanephros tissue was continued.

Figure 4:
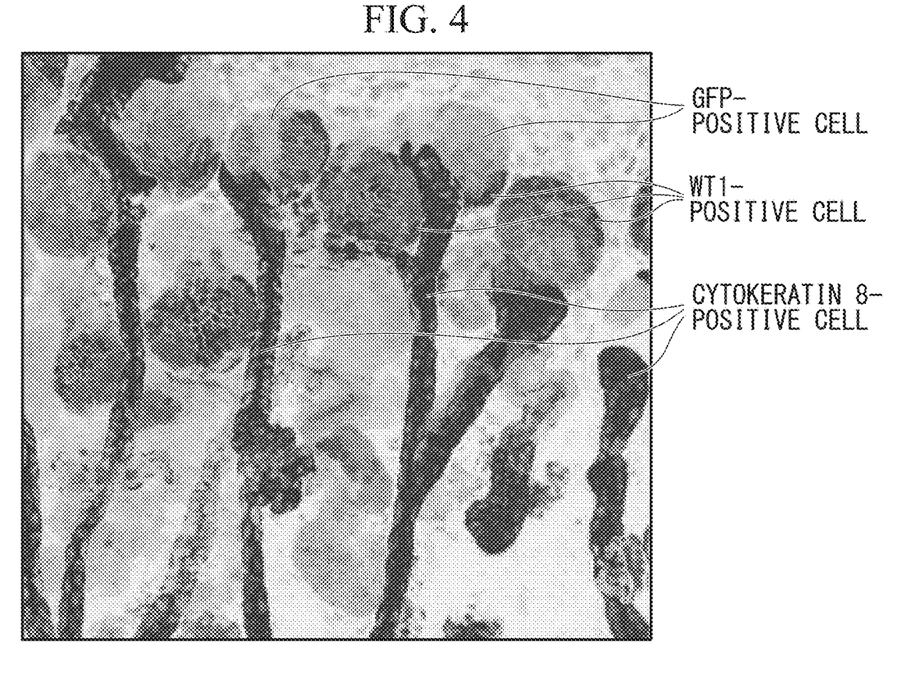
FIG. 4 is a photograph showing a result of immunostaining of a kidney tissue sample in Experimental Example 4.

Subsequently, the metanephros tissue was fixed with 4% paraformaldehyde after being cultured for 7 days from the transplantation of the kidney precursor cells, and therefore a tissue section sample was prepared. Subsequently, cytokeratin 8, which is a marker for the ureteric bud, and Wilms tumor suppressor protein-1 (WT1), which is a marker of glomerulus, were immunostained, respectively. Subsequently, fluorescence of GFP expressing the transplanted cells, and immunostained cytokeratin 8 and WT1 was observed with a fluorescence microscope. FIG. 4 is a fluorescence microscopy photograph showing the result of immunostaining. The magnification is 200 times. In FIG. 4, GFP-positive cells and WT1-positive cells are derived from the transplanted kidney precursor cells. In addition, cytokeratin 8-positive cells are derived from the host animal ($F_1$ mouse of Experimental Example 1).

As a result, it was confirmed that the transplanted kidney precursor cells derived from the GFP tg mice formed the glomeruli and kidney tubules. This result shows that it is possible to form functional kidney tissue from the kidney precursor cells by the method described above.

Experimental Example 5

(Regeneration of Kidney in Living Body of Mouse)

In the para-aortic region of the wild-type mouse, the cloaca and the metanephros tissue-specifically expressing the diphtheria toxin receptor in the metanephros tissue, which are obtained by crossing the iDTR mouse with Six2-Cre mouse, were transplanted.

Subsequently, by administering the diphtheria toxin, the metanephric mesenchyme of the metanephros was removed, and $1 \times 10^5$ kidney precursor cells derived from the GFP tg mouse were transplanted. Subsequently, a mouse transplanted with the metanephros was raised for 7 days.

Subsequently, an abdominal cavity of the above-mentioned mouse was opened to observe the kidney (regenerated kidney) formed from the transplanted metanephros.

Figure 5A:
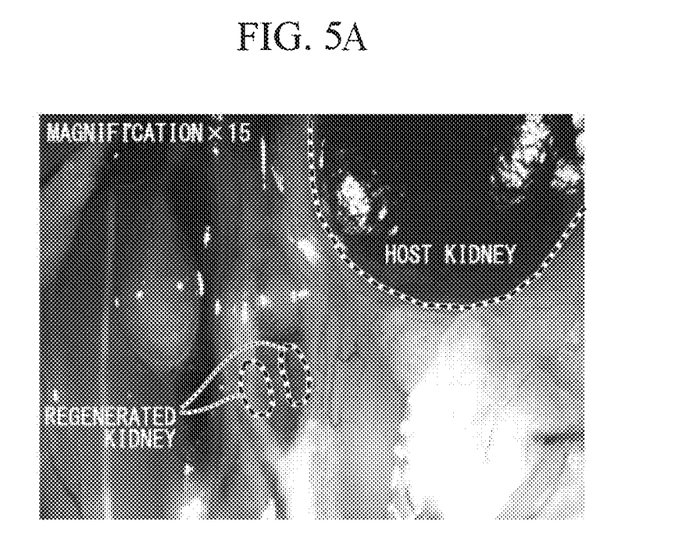
FIGS. 5A-B are photographs of a kidney regenerated in a mouse body in Experimental Example 5.

FIG. 5A is a photograph of a region where regenerated kidneys exist. The magnification is 15 times. The upper right shows the kidney of the wild-type mouse (host). The regenerated kidneys exist in a region surrounded by a dotted line near the center.

Figure 5B:
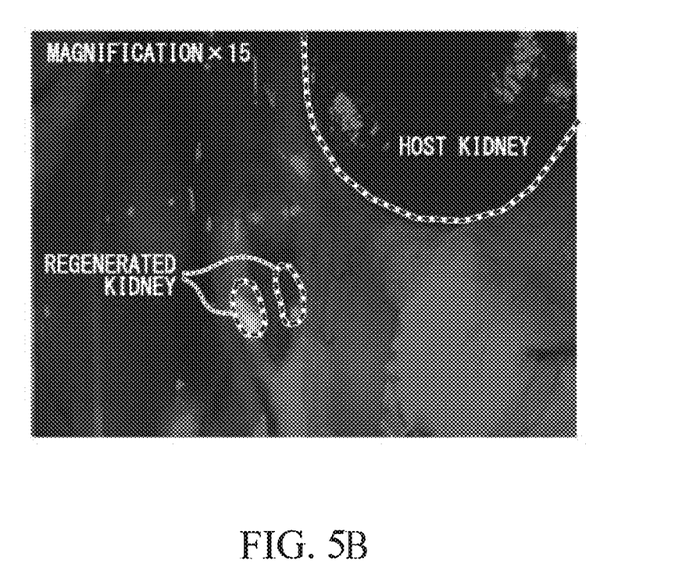

FIG. 5B is a photograph showing the observation result of the fluorescence of GFP in the same field of view as FIG. 5A. The magnification is 15 times. As a result, fluorescence of GFP derived from transplanted kidney precursor cells was observed. This result indicates that the kidney regeneration was possible in the body of the mouse.

Figure 6A:
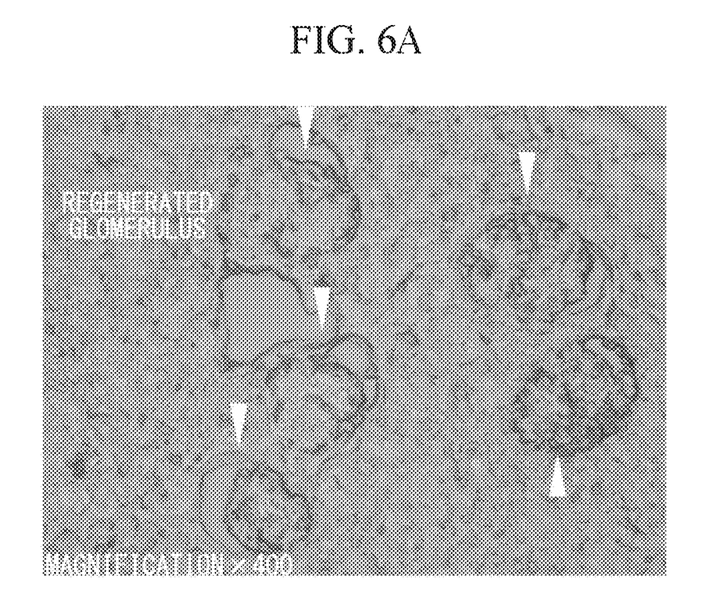
FIGS. 6A-B are microphotographs of tissue section samples of the kidney regenerated in the mouse body in Experimental Example 5.

FIG. 6A is an optical micrograph of a tissue section sample prepared by fixing the above regenerated kidneys with 4% paraformaldehyde. The magnification is 400 times. In FIG. 6A, the regenerated glomeruli were observed at a portion indicated by an arrowhead.

Figure 6B:
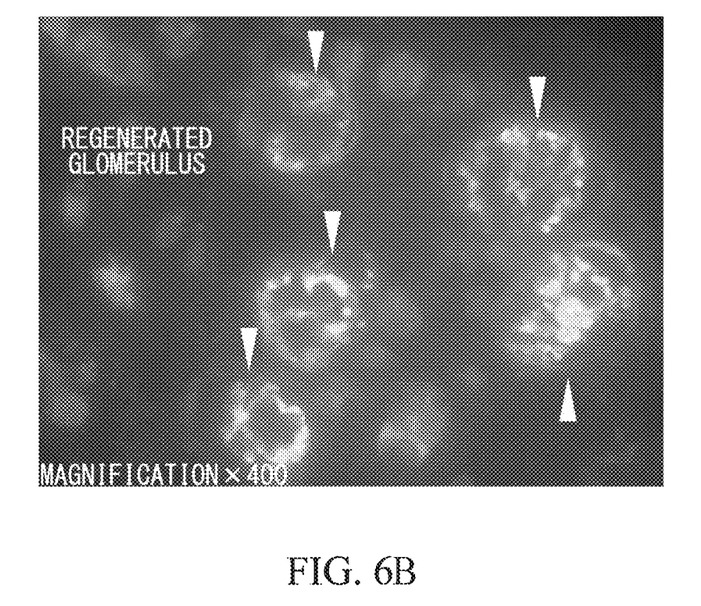

FIG. 6B is a fluorescence micrograph showing the observation result of the fluorescence of GFP in the same field of view as FIG. 6A. The magnification is 400 times. In FIG. 6B, fluorescence of GFP was observed at a portion indicated by an arrowhead. This result indicates that the regenerated glomeruli are derived from the transplanted kidney precursor cells.

Based on the above results, it became clear that the kidney regeneration can be performed in vivo.

Experimental Example 6

(Replacement of Both Metanephric Mesenchyme and Ureteric Bud of Mouse Embryo)

<<Tissue-Specific Removal of Ureteric Bud>>

In the present experimental example, the iDTR mouse having a genotype of Six2-Cre-ER$^{tg/wt}$HoxB7-Cre$^{tg/wt}$ was used. First, in the same manner as in Experimental Example 1, the metanephros was extracted from the mouse embryo and subjected to organ-culture. Subsequently, diphtheria toxin was added to the medium to tissue-specifically remove the ureteric bud.

<<Transplantation of Kidney Precursor Cells>>

Subsequently, in the same manner as in Experimental Example 2, $1 \times 10^5$ kidney precursor cells derived from the wild-type mouse were transplanted into the metanephros of the mouse, from which the ureteric bud was removed. Thereafter, the organ culture of the metanephros was continued for 5 days.

<<Tissue-Specific Removal of Metanephric Mesenchyme>>

Subsequently, tamoxifen and diphtheria toxin were added to the culture medium for organ culture. As a result, in the Six2-expressing cell, which is a metanephric mesenchyme-specific marker, Cre-ER is translocated into the nucleus and recombines to express the diphtheria toxin receptor. As a result, cells of the metanephric mesenchyme were killed by diphtheria toxin. As a result, the metanephric mesenchyme was tissue-specifically removed.

<<Transplantation of Kidney Precursor Cells>>

Subsequently, in the same manner as in Experimental Example 2, $1 \times 10^5$ kidney precursor cells derived from the wild-type mouse were transplanted again into the metanephros of the mouse, from which the metanephric mesenchyme was removed. Thereafter, the organ culture of the metanephros was continued for 3 to 5 days.

<<Immunostaining>>

Subsequently, the metanephros after organ culture was fixed with 4% paraformaldehyde, and therefore a tissue section sample was prepared. Subsequently, the metanephros was immunostained with an anti-calbindin antibody for staining the ureteric bud and observed with a fluorescence microscope.

Figure 7A:
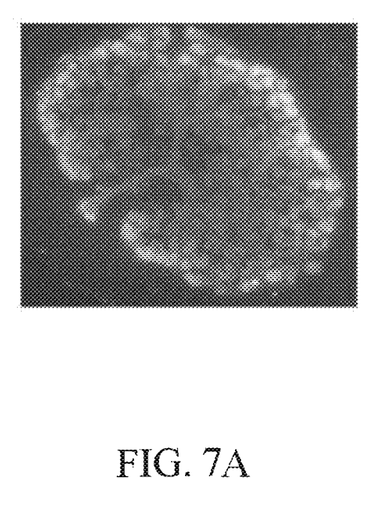
FIGS. 7A-C are photographs showing results of immunostaining of a tissue sample of a metanephros in Experimental Example 6.

FIG. 7A is a representative photograph of the metanephros of a positive control. For the positive control, the diphtheria toxin was not added in the stage of removing the ureteric bud, and the kidney precursor cells were not transplanted. Therefore, in the positive control, tissues derived from the original ureteric bud were maintained.

Figure 7B:
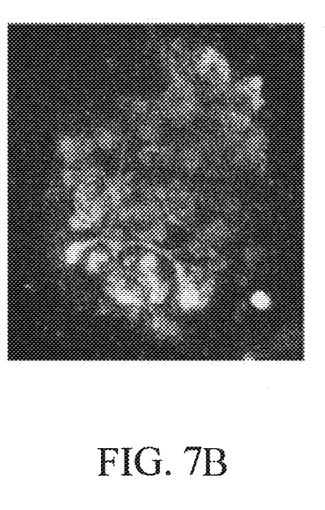

FIG. 7B is a representative photograph of the metanephros of a negative control. For the negative control, the diphtheria toxin was added in the stage of removing the ureteric bud, and the kidney precursor cells were not transplanted. Accordingly, because in the negative control, the ureteric bud was tissue-specifically removed, and the kidney precursor cells were not transplanted, the ureteric bud was lost.

Figure 7C:
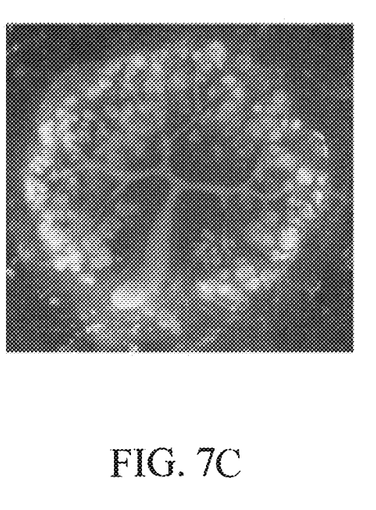

FIG. 7C is a representative photograph of the metanephros of a test group. In the test group, the ureteric bud was tissue-specifically removed, and the kidney precursor cells were transplanted. As a result, the ureteric bud was replaced by the transplanted kidney precursor cells, and the growth of tissues derived from the ureteric bud was observed.

Table 1 shows the results of measuring the number of ureteric bud tips in the metanephros of the positive control (n=5), the negative control (n=5), and the test group (n=5).

TABLE 1

|  | Positive control | Negative control | Test group |
|---|---|---|---|
| Number of ureteric bud tips (average value ± standard deviation) | 145.2 ± 22.2 | 73.2 ± 29.2 | 120.8 ± 23.8 |

As a result, in the negative control, a decrease in the number of ureteric bud tips was observed compared to the positive control. In contrast, in the test group, the same number of ureteric bud tips as the positive control was measured. This result shows that both metanephric mesenchyme and ureteric bud can be replaced with the transplanted kidney precursor cells by the method of the present experimental example.

INDUSTRIAL APPLICABILITY

According to the present invention, it is possible to provide a technique for producing a kidney from kidney precursor cells.

The invention claimed is:
1. A kidney production method comprising:
(i) tissue-specifically removing kidney precursor cells in a metanephric mesenchyme of a metanephros of a non-human animal;
(ii) transplanting a human kidney precursor cell into the metanephros; and
(iii) advancing development of the metanephros, wherein the transplanted human kidney precursor cell is differentiated and metanephric mesenchyme is regenerated,
(iv) tissue-specifically removing kidney precursor cells in a ureteric bud of the metanephros;
(v) transplanting a human kidney precursor cell into the metanephros;
(vi) advancing development of the metanephros, wherein the transplanted kidney precursor cell is differentiated and ureteric bud is regenerated; and
(vii) forming a kidney by advancing development of the metanephros,
wherein (i) to (vii) are performed in an order of (i), (ii), (iii), (iv), (v), (vi), (vii) or in an order of (iv), (v), (vi), (i), (ii), (iii), (vii).
2. The kidney production method according to claim 1, wherein the non-human animal is a pig.
3. The kidney production method according to claim 1, wherein the non-human animal is a mouse.

* * * * *